United States Patent
Brunet et al.

(10) Patent No.: US 11,156,558 B2
(45) Date of Patent: Oct. 26, 2021

(54) ASSESSMENT OF STABILITY OF BIOLOGICAL PRODUCT IN PREFILLED SYRINGES

(71) Applicant: Becton Dickinson France, Le Pont de Claix (FR)

(72) Inventors: Claire Brunet, Grenoble (FR); Jean-Bernard Hamel, Saint Cassien (FR)

(73) Assignee: Becton Dickinson France, Le Pont de Claix (FR)

( * ) Notice: Subject to any disclaimer, the term of this patent is extended or adjusted under 35 U.S.C. 154(b) by 405 days.

(21) Appl. No.: 16/349,761

(22) PCT Filed: Nov. 7, 2017

(86) PCT No.: PCT/EP2017/078452
§ 371 (c)(1),
(2) Date: May 14, 2019

(87) PCT Pub. No.: WO2018/091314
PCT Pub. Date: May 24, 2018

(65) Prior Publication Data
US 2019/0383749 A1   Dec. 19, 2019

(30) Foreign Application Priority Data
Nov. 15, 2016   (EP) .................................... 16306490

(51) Int. Cl.
*G01N 21/77*   (2006.01)
*G01N 30/06*   (2006.01)
*G01N 33/68*   (2006.01)
*C07K 7/06*   (2006.01)
*G01N 30/72*   (2006.01)
*G01N 30/02*   (2006.01)

(52) U.S. Cl.
CPC ............... *G01N 21/77* (2013.01); *C07K 7/06* (2013.01); *G01N 30/06* (2013.01); *G01N 30/7233* (2013.01); *G01N 33/68* (2013.01); *G01N 2030/027* (2013.01)

(58) Field of Classification Search
CPC .... G01N 21/77; G01N 30/06; G01N 30/7233; G01N 33/68; G01N 2030/027; G01N 30/72; C07K 7/06
See application file for complete search history.

(56) References Cited

PUBLICATIONS

Hoofnagle et al., "Recommendations for the generation, quantification, storage, and handling of peptides used for mass spectrometry-based assays", Clinical Chemistry 2016 (Year: 2016).*
Akala et al., "Effect of packaging on stability of drugs and drug products contents", 2008.

(Continued)

*Primary Examiner* — Jennifer Wecker
*Assistant Examiner* — Michael Paul Shimek
(74) *Attorney, Agent, or Firm* — The Webb Law Firm

(57) ABSTRACT

Provided herein is a method to mimic and assess the chemical degradation risk of a biological product, in pre-filled syringes (PFS), using a custom-designed mimetic peptide. Such method is also able to predict the susceptibility to degradation of biological product in solution in a container for medical usage.

15 Claims, 4 Drawing Sheets
Specification includes a Sequence Listing.

Coated Plunger Stopper

Non-coated Plunger Stopper (56) References Cited

PUBLICATIONS

Alston et al., "Tryptophan fluorescence reveals the presence of long-rane interactions in the denatured state of ribonuclease", Sa. Biophysical Journal, 2008, vol. 94, No. 6, pp. 2288-2296.

Blessy et al., "Development of forced degradation and stability indicating studies of drugs—A review", Journal of Pharmaceutical Analysis, 2014. vol. 4, No. 3, pp. 159-165.

Disa et al., "Investigations of the mechanism of the proline effect in tandem mass spectrometry experiments: the pipecolic", Ac. Journal of the American Society for Mass Spectrometry, 2014, vol. 25, No. 10, pp. 1705-1715.

Hoofnagle et al., "Recommendations for the generation, quantification, storage, and handling of peptides used for mass spectrometry-based assays", Clinical Chemistry 2016.

Majumdar et al., "Evaluation of the effect of syringe surfaces on protein formulations", Journal of Pharmaceutical Sciences, 2011, vol. 100, No. 7, pp. 2563-2573.

Yoshioka, "Stability of dosage forms In: Stability of Drugs and Dosage Forms", Kluwer Academic Publishers, 2002, pp. 151-186.

\* cited by examiner

Figure 1

*Coated Plunger Stopper*

*Non-coated Plunger Stopper*

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: synthesized pentapeptide

<400> SEQUENCE: 1

Ala Ala Trp Ala Ala
1               5

<210> SEQ ID NO 2
<211> LENGTH: 5
<212> TYPE: PRT
<213> ORGANISM: Artificial Sequence
<220> FEATURE:
<223> OTHER INFORMATION: synthesized pentapeptide

<400> SEQUENCE: 2

Ala Ala His Ala Ala
1               5

<210> SEQ ID NO 3
<211> LENGTH: 5
<212> TYPE: PRT
<213> ORGANISM: Artificial Sequence
<220> FEATURE:
<223> OTHER INFORMATION: synthesized pentapeptide

<400> SEQUENCE: 3
```

```
Ala Ala Met Ala Ala
1               5

<210> SEQ ID NO 4
<211> LENGTH: 5
<212> TYPE: PRT
<213> ORGANISM: Artificial Sequence
<220> FEATURE:
<223> OTHER INFORMATION: synthesized pentapeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Ala Ala Xaa Ala Ala
1               5
```

ASSESSMENT OF STABILITY OF BIOLOGICAL PRODUCT IN PREFILLED SYRINGES

CROSS-REFERENCE TO RELATED APPLICATIONS

This application is the United States national phase of International Application No. PCT/EP2017/078452 filed Nov. 7, 2017, and claims priority to European Patent Application No. 16306490.0 filed Nov. 15, 2016, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1902499_ST25.txt. The size of the text file is 1,086 bytes, and the text file was created on Apr. 30, 2019.

FIELD OF THE INVENTION

The technical domain of the invention is the assessment of stability of biological product in prefilled syringes (PFS).

The invention relates to a method to determine the chemical degradation risk of a biological product, the degradation occurring mainly by contact, in particular long term contact, with part of a container for medical usage, for example a syringe and the biological product comprising at least one amino acid chosen among methionine, tyrosine, tryptophan, histidine, glutamine, asparagine, cysteine, arginine, aspartate, glutamate, lysine, proline, serine, threonine and phenylalanine.

It is well known that development and manufacturing of pharmaceutical drug product are challenging due to the regulations, safety and quality requirements. In particular, the risk of contaminating patients with contaminating compounds to should be managed and controlled to assess quality risk management.

The risk of contaminating compounds increases when the pharmaceutical drug product is in solution in a container for medical usage, the typical one being a prefilled syringe containing, for example, a vaccine. The contaminating compounds are inevitable when one considers all the polymeric surfaces that a drug substance or drug product comes into direct and/or indirect contact with throughout manufacturing, filling, packaging and labeling, storage and transportation. Sources of contaminating compounds can come from the part of a container (examples are glass barrel, stainless steel hypodermic needle, rubber needle shield, silicone oil lubricants and rubber plunger stopper) and other surprising sources are from residues from processing tools and additives for attaching the needle to the barrel and more generally speaking from the part of a container for medical usage.

The contaminating compounds may enhance immunogenicity, either by chemically modifying the therapeutic biological product or by having direct immune adjuvant activity.

Consequently, there was a need to predict the risk of contaminating compounds release by a container for medical usage faced to the biological product stored for a long time. Consequently, drug delivery device suppliers and drug manufacturers conducted extractable and leachable studies to predict and assess the nature of those contaminating compounds that may leach into the container and get into contact with biological product. The Product Quality Research Institute (PORI) has made a significant contribution towards best practices for extractables and leachables (E&Ls) assessments in orally inhaled nasal drug products OINDPs and is currently focusing on the parenteral and ophthalmic drug products (PODPs) to classify the leachables into genotoxicants, irritants, sensitizers, and other toxicants, with a proposed threshold for each class. Subject to the validation of this classification scheme and a dataset large enough for statistical analysis, contaminating compound will be considered for qualification on the basis of their respective thresholds.

However, there is a need for a coherent scientific frame, able to understand the potential of a contaminating compound to interact with biological product and causes chemical degradation.

To assess the suitability of a prefilled syringe (PFS) system for development of a monoclonal antibody (mAb) product, a known experimental approach has been developed consisting in the following assessment of the integrity of an entire biological product when putted in contact with prefilled syringe components during a minimum of a 6-month accelerated stability study. This approach highlights the potential of leachables to interact with biological products but the unique nature of each protein makes this study very specific and constrains pharmaceutical manufacturers to perform this type of long and expensive study for each biological product under development.

Another known experimental approach has been developed showing an important interest on biological products which are susceptible to leachate-induced structural modifications and propose a holistic extractables and leachables program for biotechnology product. This method identified the compounds which can potentially form covalent modifications of proteins and they have established a decision tree for science- and risk-based analysis of extractables and leachables profile. However, this approach requires to discover, identify and quantify all potential extractables and leachables from any material coming from part of a container for medical usage. This information is mainly protected as know-how by the drug delivery device supplier and consequently not easily available. To obtain an exhaustive list, extractable/leachable studies have to be conducted with a panel of analytical techniques and exhaustive screening methods and associated expertise in chemical structural identification.

Thus, there is an ongoing need in the art to optimize science based methods to de-risk long-term stability of biological product in container for medical usage, like prefilled syringes.

Surprisingly, the inventors have found that the use of a mimetic model peptide could meet this requirement. Using a custom-designed mimetic peptide, the inventors have developed a method to mimic and assess the chemical degradation of a biological product when in contact with part of a container for medical usage. Such method is also able to predict the susceptibility to degradation of biological product in solution in a container for medical usage.

In this context, the invention relates to a method to determine the degradation percentage of a compound of formula (I) by contact with part of a container for medical usage, comprising the following successive steps:

i) preparing an aqueous solution comprising a compound of formula (I) below (I)

in which:
$R_1$, $R_2$, $R_4$ and $R_5$ each represent independently of one another H or a group (C1-C6)alkyl, (C2-C6)alkenyl or (C2-C6)alkynyl;

X represents H or a group (C1-C6)alkyl, (C2-C6) alkenyl, (C2-C6)alkynyl, (C1-C6) alkoxycarbonyl, aryl or a protecting group;

n and m each represent independently of one another an integer from 0 to 10;

R3 represents —$(CH_2)_2$—COOH, —$CH_2$—COOH, —$(CH_2)_4$—COOH, —$CH_2$—OH, —C(OH)—$CH_3$, —$CH_2$—CO—$NH_2$, $CH_2$—SH, —$(CH_2)_4$—$NH_2$, —$(CH_2)_2$—CO—$NH_2$, —$CH_2$—$CH_2$—S—$CH_3$, —$(CH_2)_3$—NH—C(NH)—$NH_2$;

or or $R_3$ represents a group of formula (II) below (II)

with $R_6$, $R_7$, $R_8$ and $R_9$ each represent independently of one another H or a group (C1-C6)alkyl, (C2-C6) alkenyl or (C2-C6)alkynyl;

X represents H or a group (C1-C6)alkyl, (C2-C6) alkenyl, (C2-C6)alkynyl, (C1-C6)alkoxycarbonyl, aryl or a protecting group;

r and p each represent independently of one another an integer from 0 to 10;

ii) adding to the solution prepared at the step i) part of a container for medical usage during a period of time of 1 hour to 2 months, at a temperature in a range from 5 to 80° C.;

iii) analyzing by liquid chromatography the solution obtained at step ii); and iv) determining the degradation percentage.

The present invention intends to provide a new method having one or more of the following characteristics:

the method according to the invention enables to mimic the degradation sensitive sites of biological products;

the method according to the invention enables to assess the susceptibility of biologicals sensitive sites to interact with part of a container for medical usage, like prefilled syringes components;

the method according to the invention enables to help biotech/drug manufacturers to make the lowest risk selection of container for medical usage and ensure predictable time-to-market;

the method according to the invention enables to assess the efficiency of pharmaceutical additives to protect the drug integrity;

the method according to the invention enables to develop methodologies and tools for fast screening interactions assessment;

the method according to the invention enables to provide accelerated stability study with model solutions in direct contact with part of a container for medical usage, process residues, mixture or individual extractable;

the method according to the invention enables to predict the risk of degradation of biological products;

the method according to the invention enables to help biotech/drug manufacturers screen and further select suitable part of containers in early drug development process;

the method according to the invention enables to help biotech/drug manufacturers in selection of the best suitable part of containers for medical usage configuration;

the method according to the invention enables to understand interaction issues for biological product in prefilled container for medical usage for post market investigations;

the method according to the invention enables to evaluate the new part of a container;

the method according to the invention enables to select the best suitable part of a container;

the method according to the invention enables to control and assess change consequence of part of a container.

Definitions

By the term "part of a container" used in the expression "part of a container for medical usage", it is understood either the whole container itself, a portion of the container, an element of the container or the raw material used to manufacture the container, or even contaminating compounds. A container of the present invention is not limited by material of manufacture, and includes many materials such as glass, metals (e.g., steel, stainless steel, aluminum, etc.), polymers (e.g., thermoplastics, elastomers, thermoplastic-elastomers) and silicone oil lubricants. The common polymers include polyethylene (PE), polypropylene (PP), polycarbonate (PC), fluorinated ethylene-propylene (FEP), ethylene tetrafluoroethylene (ETFE) and polytetrafluoroethylene (PTFE). The common elastomers include saturated and unsaturated elastomers: bromobutyl elastomer, chlorobutyl isoprene blend, natural rubber and synthetic polyisoprene rubber, butyl rubber and halogenated butyl rubber, styrene-butadiene rubber, nitrile rubber, ethylene propylene rubber (EPM), and ethylene propylene diene rubber, Polyacrylic rubber, Silicone rubber, Fluorosilicone Rubber, Fluoroelastomers, Perfluoroelastomers, Polyether block amides, Chlorosulfonated polyethylene, Ethylene-vinyl acetate etc.

It is understood that part of a container for medical usage may content contaminating compounds.

Others materials are polyester, poly-vinylidene dichloride (PVDC), ethyl vinyl alcohol (EVOH), copolymer, polyamide (PA), polyethylene terephthalate (PET), polydimethylsiloxanes (PDMSs) and polysulfone (PS).

The common metals include chromium, copper, iron, manganese, nickel, tungsten, and zinc, lithium, boron, magnesium, aluminum, silicon, titanium, chrome, cobalt, arsenic, antimony, barium and their oxidative derivatives.

By the expression "container for medical usage", it is understood any means which is used to "contain", "hold", "mix", "blend", "dispense", "inject", "transfer", "nebulize", etc. a biological product during research, processing, development, formulation, manufacture, storage and/or administration. For example, the container for medical usage of the present invention includes, but is not limited to, general laboratory glassware, flasks, beakers, graduated cylinders, fermentors, bioreactors, tubings, pipes, bags, single-use biomass bag, jars, vials, vial closures (e.g., a rubber stopper, a screw on cap), ampoules, syringes, prefilled syringes, prefillable syringes, auto-injectors, pen-injectors, stoppers, syringe stoppers, syringe plungers, rubber closures, plastic closures, glass closures, barrels, tip caps, caps, needles, plungers, plunger stoppers, plunger rods, glass barrels, stainless steel hypodermic needles, rubber needle shields, coated rubber plunger stopper, adhesive's labels, ink's labels, coating's labels and the like. Additional container for medical usage contemplated in the present invention may be found in published catalogues from laboratory equipment vendors and manufacturers such as VWR™ (West Chester, Pa.), BD Biosciences (Franklin Lakes, N.J.), Fisher Scientific International Inc. (Hampton, N.H.) and Sigma-Aldrich (St. Louis, Mo.).

By the expression "prefilled syringe", it is understood a syringe already prefilled with a fluid, also abbreviated by PFS.

By the expression "prefillable syringe" it is understood an empty syringe able to be filled.

By the expression "syringe" it is understood either a prefilled or prefillable syringe.

By the expression "drug delivery device supplier" it is understood a supplier part of a container for medical usage.

As defined herein, a "biological product" of the present invention includes peptides, proteins, polysaccharide-protein conjugate, protein-based biopharmaceutical product, drug products for human and/or animal use. Most of the time, the biological product could be an Active Pharmaceutical Ingredient (API). An API is intended to provide pharmacological activity or other direct effect in the diagnosis, cure, mitigation, treatment, or prevention of disease or to affect the structure or any function of the body of men or animals.

By the term "degradation" or "chemical degradation", it is understood a chemical modification of biological products due to reaction with components in the environment, in particular with contaminating compounds. Generally, these modifications occur with the most reactive side chains and are predominantly oxidations, reductions and nucleophilic and electrophilic substitutions.

Degradations include peptide bond scissions, racemizations, 6-eliminations, and formations of products by the reaction of proteins with added chemicals. Degradations exclude natural conformational change, native structure change like electrostatic interaction, hydrophobic interaction etc.

By the term "stability", it is understood chemical stability, since no chemical degradation of a biological product occurs. The primary structure of the biological product remains unchanged along the storage in a container for medical usage or along the contact with part of a container for medical usage.

As set forth herein, the term "contaminating compounds" is intended to cover contaminating compounds that include extractables, leachables or process residues.

Extractables are compounds that can be extracted from part of a container for medical usage, like elastomeric or plastic components, extracted in the presence of a solvent, in particular under harsh conditions. The extractables could be complex mixtures consisting primarily of oligomers and additives of diverse physical and chemical properties and are often present in concentrations much lower than any other ingredient of the biological product, making detection of their presence difficult. The American Food & Drug Administration (FDA) requires evaluation of the extractables for their impact on the safety and efficacy of the biological products.

Leachables are compounds that leach into the formulation from part of a container for medical usage, like elastomeric or plastic components, in particular under real-use conditions. Examples of leachables include but is not limited to acrylic acid, methacrylic acid, 1,6-hexanediol diacrylate, and dibutylmaleate. The impact of leachables on biological product can be related to degradation, aggregation, particle formation, and/or product quality issues such as reaction with the formulation or protein.

By the term "process residues", it is understood chemical compounds coming from the container for medical usage or coming from injectable drug product manufacturing or filling processes. As example of process residues, it could be listed: surfactants, tungsten, organic acids without being limited by this list.

The term "(C1-C6)alkyl", as used in the present invention, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "(C2-C6)alkenyl", as used in the present invention, refers to a straight or branched monovalent unsaturated hydrocarbon chain containing from 2 to 6 carbon atoms and comprising at least one double bond including, but not limited to, ethenyl, propenyl, butenyl, pentenyl, hexenyl and the like.

The term "(C2-C6)alkynyl", as used in the present invention, refers to a straight or branched monovalent unsaturated hydrocarbon chain containing from 2 to 6 carbon atoms and comprising at least one triple bond including, but not limited to, ethynyl, propynyl, butynyl, pentynyl, hexynyl and the like.

The term "(C1-C6)alkoxy", as used in the present invention, refers to a (C1-C6)alkyl group as defined above, bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "(C1-C6)alkoxycarbonyl", as used in the present invention, refers to a (C1-C6)alkoxy group as defined above bound to the molecule via a —C(=O)— group, including, but not limited to ethoxycarbonyl, methoxycarbonyl, and t-butyloxycarbonyl (Boc).

The term "aryl", as used in the present invention, refers to an aromatic hydrocarbon group comprising preferably 6 to 10 carbon atoms and comprising one or more fused rings, such as, for example, a phenyl or naphtyl group. Advantageously, it will be a phenyl group.

The term "protecting group", as used in the present invention, refers to a chemical group which selectively blocks a reactive site in a multifunctional compound so as to allow selectively performing a chemical reaction on another unprotected reactive site.

The term "O-protecting group" as used in the present invention refers to a substituent which protects hydroxyl groups (OH) of the compounds of formula (I) against undesirable reactions during synthetic procedures such as those O-protecting groups disclosed in "Greene's Protective Groups In Organic Synthesis", 4th edition, 2007, John Wiley & Sons, Hoboken, N.J. Usually, the group OX of the compounds of formula (I) is capped with such a protecting group in order to protect the hydroxyl function. A hydroxyl group protected by a O-protecting group can be for example an ether, an ester, a carbonate, an acetal and the like. In particular, O-protecting groups can be a (C1-C6)alkyl optionally substituted with one or several (notably 1 to 3) halogen atoms (such as chlorine atoms), such as methyl, ethyl, tert-butyl or 2,2,2-trichloroethyl; an aryl-(C1-C6) alkyl, such as a benzyl, the aryl moiety being optionally substituted with one or several methoxy groups, such as benzyl (Bn) or p-methoxybenzyl (PMB); a trityl derivative of formula —CAr1Ar2Ar3 such as triphenylmethyl (also called trityl—Tr), (4-methoxyphenyl)diphenylmethyl (also called methoxytrityl—NMT) or bis-(4-methoxyphenyl)phenylmethyl (also called dimethoxytrityl—DMT); a substituted methyl group of formula CH2ORGP2 or CH2SRGP2 (in particular CH2ORGP2), for example, methoxymethyl (MOM), benzyloxymethyl, 2-methoxyethoxymethyl (MEM), 2-(trimethylsilyl)ethoxymethyl or methylthiomethyl; a substituted ethyl group of formula CH2CH2ORGP2 or CH2CH2SRGP2 (in particular —CH2CH2ORGP2), for example, ethoxyethyl (EE); a silyl group of formula —SiRGP3RGP4RGP5, for example, trimethylsilyl (TMS), triethylsilyl (TES), t-butyldimethylsilyl (TBS or TBDMS) and t-butyldiphenylsilyl (TBDPS); a carbonylated group of formula CO-RGP6 such as acetyl (Ac), pivaloyl (Piv or Pv) or benzoyl (Bz) or of formula —CO2-RGP7 such as allyloxycarbonyl (Alloc) or 9-fluorenylmethyloxycarbonyl (Fmoc); or a tetrahydropyranyl (THP) or tetrahydrofuranyl group;
with Ar1, Ar2 and Ar3 representing, independently from one another, an aryl, such as a phenyl, optionally substituted with one or several methoxy groups; RGP2 representing a (C1-C6)alkyl (such as methyl or ethyl) optionally substituted with an aryl (such as phenyl), a (C1-C6)alkoxy (such as methoxy) or a trialkylsilyl group (such as SiMe3); RGP3, RGP4 and RGP5 representing, independently from one another, a (C1-C6)alkyl or aryl (such as phenyl) group; and RGP6 and RGP7 representing, independently of each other, a (C1-C6)alkyl, a (C2-C6)alkenyl, an aryl, an aryl-(C1-C6) alkyl or a 9-fluorenylmethyl group.

In particular, it will be a benzyl, acetyl or methoxymethyl group.

The term "N-protecting group", as used in the present invention, serves principally to control the synthesis of the compound of formula (I). For this purpose, all moieties typically used in peptide chemistry, as protecting groups in general, are suitable. Usually, the amino group $X_2N$ of the compound of formula (I) is capped with such a protecting group in order to protect the amine function against undesirable reactions during synthetic procedures. Commonly used N-protecting groups are disclosed in "Greene's Protective Groups In Organic Synthesis", 4th edition, 2007, John Wiley & Sons, Hoboken, N.J. The $X_2N$ amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups can be formyl; an aryl, such as phenyl, optionally substituted with one or several methoxy groups such as p-methoxyphenyl (PMP); an aryl-(C1-C6) alkyl, such as a benzyl, the aryl moiety being optionally substituted with one or several methoxy groups, such as benzyl (Bn), p-methoxybenzyl (PMB) or 3,4-dimethoxybenzyl (DMPM); CO-RGP1 such as acetyl (Ac), pivaloyl (Piv or Pv), benzoyl (Bz) or p-methoxybenzylcarbonyl (Moz); —CO2-RGP1 such as tbutyloxycarbonyl (Boc), trichloroethoxycarbonyl (TROC), allyloxycarbonyl (Alloc), benzyloxycarbonyl (Cbz or Z) or 9-fluorenylmethyloxycarbonyl (Fmoc); —SO2-RGP1 such as phenylsulfonyl, tosyl (Ts or Tos) or 2 nitrobenzenesulfonyl (also called nosyl—Nos or Ns); and the like,
with RGP1 representing a (C1-C6)alkyl optionally substituted with one or several halogen atoms such as F or Cl; a (C2-C6)alkenyl such as an allyl; an aryl, such as a phenyl, optionally substituted with one or several groups chosen among OMe (methoxy) and NO2 (nitro); an aryl-(C1-C6) alkyl, such as a benzyl, the aryl moiety being optionally substituted with one or several methoxy groups; or a 9-fluorenylmethyl group.

In particular, it can be a tert-butyloxycarbonyl (Boc), benzyloxycarbonyl (Cbz) or 9-fluorenylmethyloxycarbonyl group (Fmoc).

By the term "liquid chromatography", as used in the present invention, refers to analytical techniques using a liquid chromatography apparatus used to separate compounds coupled with a detector employed to detect the degradation products of the formula (I) and the presence of contaminating compounds. The liquid chromatography apparatus could be chosen among HPLC (high performance liquid chromatography), UPLC (ultra-performance liquid chromatography), UHPLC (ultrahigh-performance liquid chromatography) and RRLC (Rapid Resolution Liquid Chromatography. The detector could be chosen among UV detector, diode array detector (DAD), mass spectrometer (MS), photodiode array detector (PDA) combined with a mass spectrometer (PDA/MS or DAD/MS), evaporative light-scattering detection (ELSD) and corona CAD detector.

DESCRIPTION OF THE INVENTION

The invention relates to a method to determine the degradation percentage of a compound of formula (I) by contact with part of a container for medical usage, comprising the following successive steps:

i) preparing an aqueous solution comprising a compound of formula (I) below (I)

in which:

$R_1$, $R_2$, $R_4$ and $R_5$ each represent independently of one another H or a group (C1-C6)alkyl, (C2-C6)alkenyl or (C2-C6)alkynyl;

X represents H or a group (C1-C6)alkyl, (C2-C6) alkenyl, (C2-C6)alkynyl, (C1-C6) alkoxycarbonyl, aryl or a protecting group;

n and m each represent independently of one another an integer from 0 to 10;

R3 represents —(CH$_2$)$_2$—COOH, —CH$_2$—COOH, —(CH$_2$)$_4$—COOH, —CH$_2$—OH, —C(OH)—CH$_3$, —CH$_2$—CO—NH$_2$, CH$_2$—SH, —(CH$_2$)$_4$—NH$_2$, —(CH$_2$)$_2$—CO—NH$_2$, —CH$_2$—CH$_2$—S—CH$_3$, —(CH$_2$)$_3$—NH—C(NH)—NH$_2$;

or $R_3$ represents a group of formula (II) below (II)

with $R_6$, $R_7$, $R_8$ and $R_9$ each represent independently of one another H or a group (C1-C6)alkyl, (C2-C6) alkenyl or (C2-C6)alkynyl;

X represents H or a group (C1-C6)alkyl, (C2-C6) alkenyl, (C2-C6)alkynyl, (C1-C6)alkoxycarbonyl, aryl or a protecting group;

r and p each represent independently of one another an integer from 0 to 10;

ii) adding to the solution prepared at the step i) part of a container for medical usage during a period of time of 1 hour to 2 months, at a temperature in a range from 5 to 80° C.;

iii) analyzing by liquid chromatography the solution obtained at step ii); and iv) determining the degradation percentage.

According to the method of the invention, the contact with part of a container for medical usage could be either direct or indirect. By direct contact, it means that the biological product is contacting part of the container without any intermediate. By indirect contact, it means that the biological product is never contacting part of the container, but is contacting another compound/intermediate that has been in direct contact with part of the said container.

Step (i)

An aqueous solution is prepared at step i). The aqueous solution prepared at step i) comprises preferably from 30 to 100% of water, more preferably from 75 to 100%, even more preferably from 85 to 100%, mass percentage.

According to a variant, the aqueous solution prepared at step i) may further contains excipients, buffering agents, acids, bases, salts, preservatives, solubilizers, surfactants, chelating agents, sugars, amino acids, peptides, solvents and combinations thereof.

The aqueous solution prepared at step i) comprises preferably at least 5 μg/ml of compound of formula (I), more preferably at least 15 μg/ml. The amount of compound of formula (I) used at step i) depends on the sensitivity of the detector apparatus used at step iii), usually 45 μg/ml are used at step i) in order to detect the synthetized peptide degradation products.

In a preferred embodiment of the invention, the compound used at step i) is of formula (I) as defined above in which X=H.

In a preferred embodiment of the invention, the compound used at step i) is of formula (I) as defined above in which n=1 and m=1.

In a preferred embodiment of the invention, the compound used at step i) is of formula (I) as defined above in which $R_1$, $R_2$, $R_4$ and $R_5$ each represent CH$_3$, and X=H, n=1 and m=1.

In a preferred embodiment of the invention, the compound used at step i) is of formula (I) as defined above in which $R_1$, $R_2$, $R_4$ and $R_5$ each represent CH3, and X=H, n=1, m=1 and $R_3$ is one of In a preferred embodiment of the invention, the compound used at step i) is of formula (I) as defined above in which $R_1$, $R_2$, $R_4$ and $R_5$ each represent CH3, and X=H, n=1, m=1 and $R_3$ is one of:
—$CH_2$—$CH_2$—S—$CH_3$ (Met), —$(CH_2)_3$—NH—C(NH)—$NH_2$ (Arg), —$(CH_2)_4$—$NH_2$ (Lys), —$CH_2$—CO—$NH_2$ (Asn), —$CH_2$—COOH (Asp), $CH_2$—$CH_2$—CO—$NH_2$ (Gln), —$(CH_2)_2$—COOH (glu).

In a preferred embodiment of the invention, the compound used at step i) is of formula (I) as defined above in which $R_1$, $R_2$, $R_4$ and $R_5$ each represent CH3, and X=H, n=1, m=1 and $R_3$ is one of —$CH_2$—$CH_2$—S—$CH_3$, Step (ii)

During step ii), part of a container for medical usage is added to the solution prepared at step i) during a period of time of 1 hour to 2 months, at a temperature in a range from 5 to 80° C.

Preferably, step ii) occurs under partial agitation and/or into a climatic chamber.

Preferably, the part of the container for medical usage is a syringe, a prefillable syringe, part of a prefillable syringe, a prefilled syringe or part of a prefilled syringe (see definitions above).

Preferably, the part of the container for medical usage is a barrel, a tip cap, a cap, a needle or a plunger stopper, all from a syringe, a prefillable syringe or a prefilled syringe.

Preferably, the part of the container for medical usage is glass, rubber, tungsten or its derivatives, adhesive, silicon oil, plastic or metal (aluminum, boron, silicon magnesium, zinc, chrome).

The preferred duration of step ii) is in a range from 4 hours to 2 months. Most preferably, duration of step ii) is in a range from 7 days to 45 days.

The temperature of step ii) of the method according to the invention, preferably is in a range from 10 to 80° C., more preferably from 15 to 75° C., even more preferably from 18 to 70° C., even more preferably from 18 to 30° C. The temperature of step ii) of the method according to the invention, is preferably, 25° C., 45° or 70° C.

Step (iii)

At step iii), the solution obtained at step ii) is analyzed by liquid chromatography.

The preferred chromatography is the ultra-performance liquid chromatography (UPLC). The preferred detector is chosen among mass spectrometer (MS), photodiode array detector (PDA) and photodiode array detector combined with a mass spectrometer (PDA/MS). Preferably, liquid chromatography is UPLC, liquid chromatography/photodiode array detector combined with a mass spectrometer.

A PDA chromatogram is obtained in order to enable the assessment of the degradation yield of the synthetized mimetic peptide (compound of formula (I)) and to detect the related degradation products. MS spectrum is obtained in order to enable the identification of the degradation products of the compounds of formula (I).

Step (iv)

Step iv) is the determination of the degradation percentage of the compound of formula (I).

Step (v)

The method according to the invention may further comprises after step iv), a measurement step v) by mass spectrometry and a step vi) of identification of the chemical degradation, like an oxidation or deamination. MS detector can also be used for the determination of the degradation percentage of the compound of formula (I) if the compound of formula (I) co elute with a contaminating product or any compounds present in the biological product.

In the present description, including the accompanying claims, unless otherwise specified, percentages are by mass.

The following examples are provided for the invention and are purely for illustrative and non-limiting purposes.

EXAMPLES

Materials:

AAXAA (SEQ ID NO: 4) pentapeptides were synthetized by GeneCust (Luxembourg) with >99% purity. PBS (phosphate-buffered saline) and Ammonium Acetate buffer was purchased from Sigma-Aldrich (St. Louis, Mo.). All other reagents were of analytical grade.

Coating means ETFE (ethylene tetrafluoroethylene).

The peptide No. 1 was of the following formula: Ala-Ala-Trp-Ala-Ala (AAWAA) (SEQ ID NO: 1).

The peptide No. 2 was of the following formula: Ala-Ala-His-Ala-Ala (AAHAA) (SEQ ID NO: 2).

The peptide No. 3 was of the following formula: Ala-Ala-Met-Ala-Ala (AAMAA) (SEQ ID NO: 3).

The part of the container used was plunger stopper and TPE tip cap from different rubber manufacturers (such as Becton Dickinson, Aptar Stelmi, West, Sumitomo), adhesive used to stick the needle and insoluble tungsten, potential tip forming process residue.

Apparatus:

The liquid chromatography used was from Waters.

Peptide solutions were analyzed by LC/DAD/MS with Quattro premier XE Mass spectrometer from Waters.

Software used is Mass Lynx.

Example 1: Testing of a Plunger Stopper with Mimetic Peptide No. 1

The peptide AAWAA (SEQ ID NO: 1) was dissolved in ammonium acetate pH4 buffer (20 mM)+0.02% Tween 80 to a final concentration of 45 µg/ml. The obtained AAWAA (SEQ ID NO: 1) peptide solutions were stored in direct contact with a non-coated and an ETFE coated plunger stoppers for 30 days at 25° C./60% RH.

Figure 1:
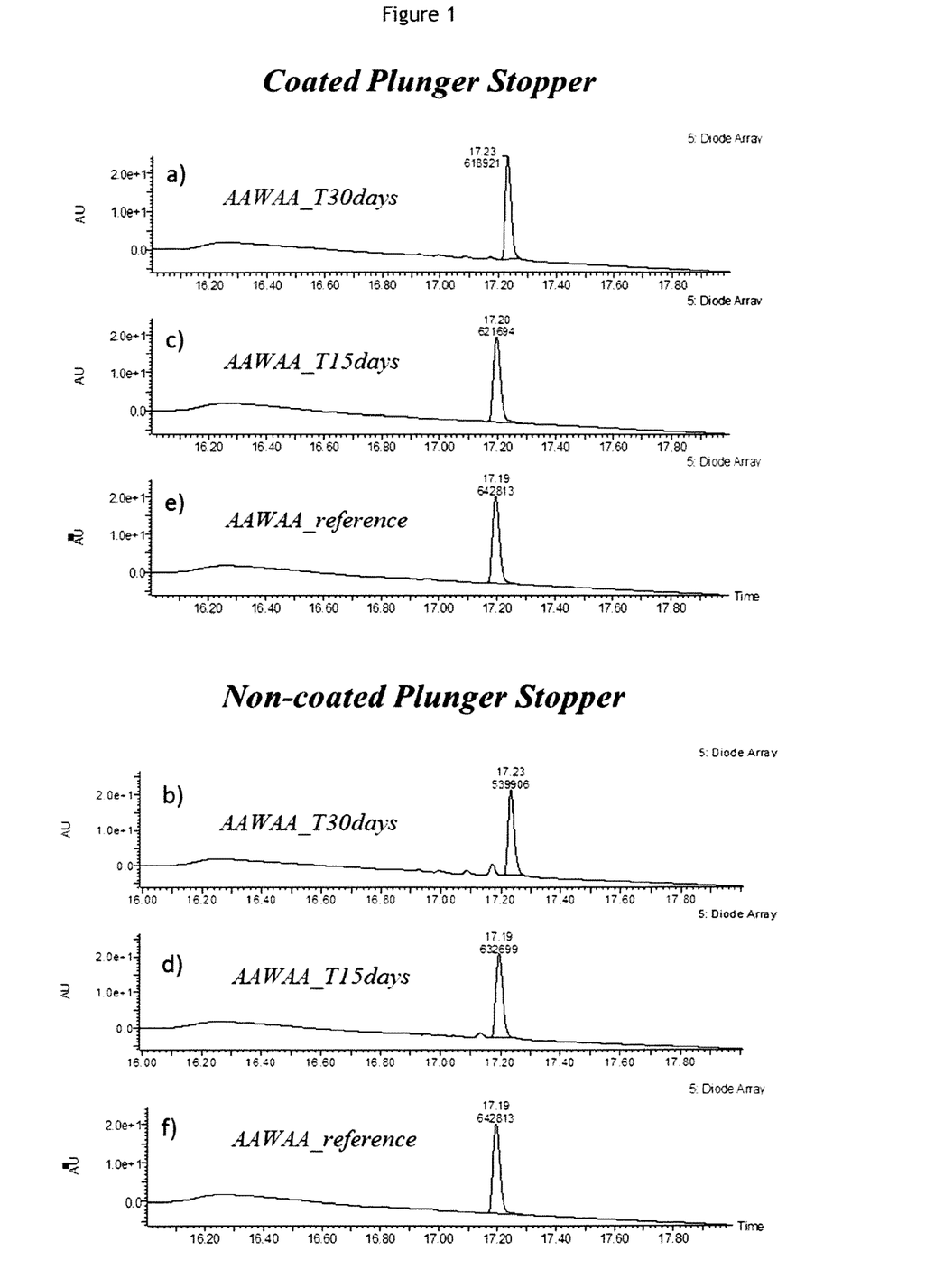
FIG. 1 is a UPLC/DAD chromatogram of AAWAA (SEQ ID NO: 1) pentapeptide after 15 or 30 days at 25° C./60% humidity relative (HR) in direct contact with a coated and a non-coated plunger stopper.
Figure 2:
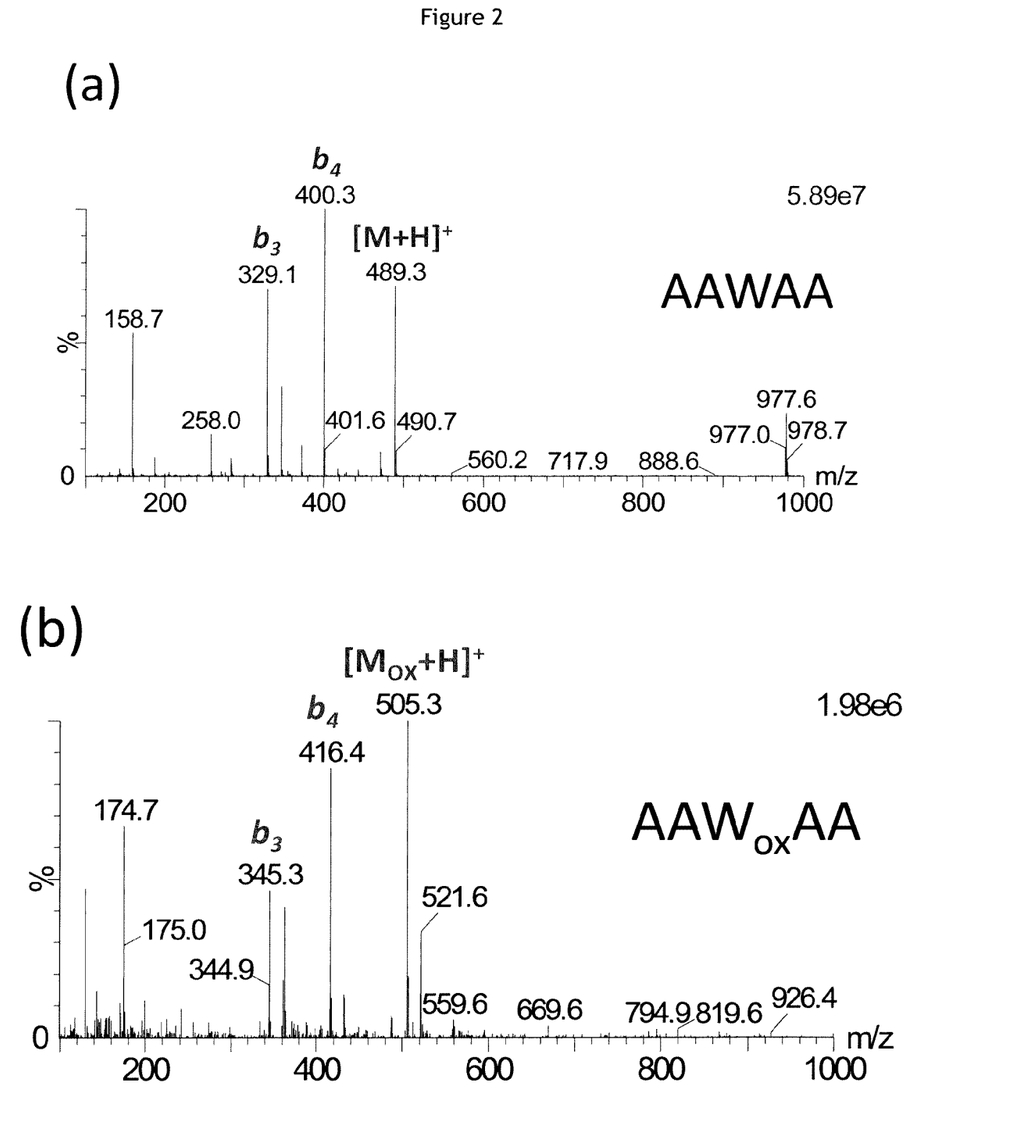
FIG. 2 is the electrospray positiv (ESI+) mass spectra of (a) intact AAWAA (SEQ ID NO: 1) peptide (Retention time of 17.2 min) and (b) oxidized form of AAWAA (SEQ ID NO: 1) (Retention time of 17.1 min) detected after 30 days (25° C.) of contact between the non-coated plunger stopper and AAWAA (SEQ ID NO: 1) peptide solution.

The results are presented on FIGS. 1 and 2.

FIG. 1 is a UPLC/DAD chromatogram of AAWAA (SEQ ID NO: 1) pentapeptide in direct contact with a coated and a non-coated plunger stopper after 15 days (c, d) and 30 days (a,b) of storage at 25° C./60% RH. Chromatograms e and f are AAWAA (SEQ ID NO: 1) solutions references (without any direct contact with plunger stoppers), FIG. 2 is the electrospray positiv (ESI+) mass spectra of (a) intact AAWAA (SEQ ID NO: 1) peptide (Retention time of 17.2 min) and (b) oxidized form of AAWAA (SEQ ID NO: 1)(Retention time of 17.1 min) detected after 30 days (25° C.) of contact between the non-coated plunger stopper and AAWAA (SEQ ID NO: 1) peptide solution.

As observed on FIG. 1 (a and b), degradation yield of AAWAA (SEQ ID NO: 1) is more important when the peptide is in direct contact with the non-coated plunger stopper. AAWAA (SEQ ID NO: 1) degradation products are observed on FIG. 1b. The higher degradation yield of AAWAA (SEQ ID NO: 1) when stored in direct contact with the non-coated stopper highlights higher risks of W amino acid and leachable interactions.

Example 2: Testing of Adhesive and Tungsten Residue with Mimetic Peptide No. 2 at High Temperature and Short Duration Time The AAHAA (SEQ ID NO: 2) peptide was dissolved in ammonium acetate pH4 buffer (20 mM)+0.02% of tween 80 to a final concentration of 45 µg/ml. The AAHAA (SEQ ID NO: 2) peptide solution was stored in direct contact with the adhesive used to stake the needle to the syringe and with insoluble tungsten, a potential process residue, for 3 days at 70° C.

Figure 3:
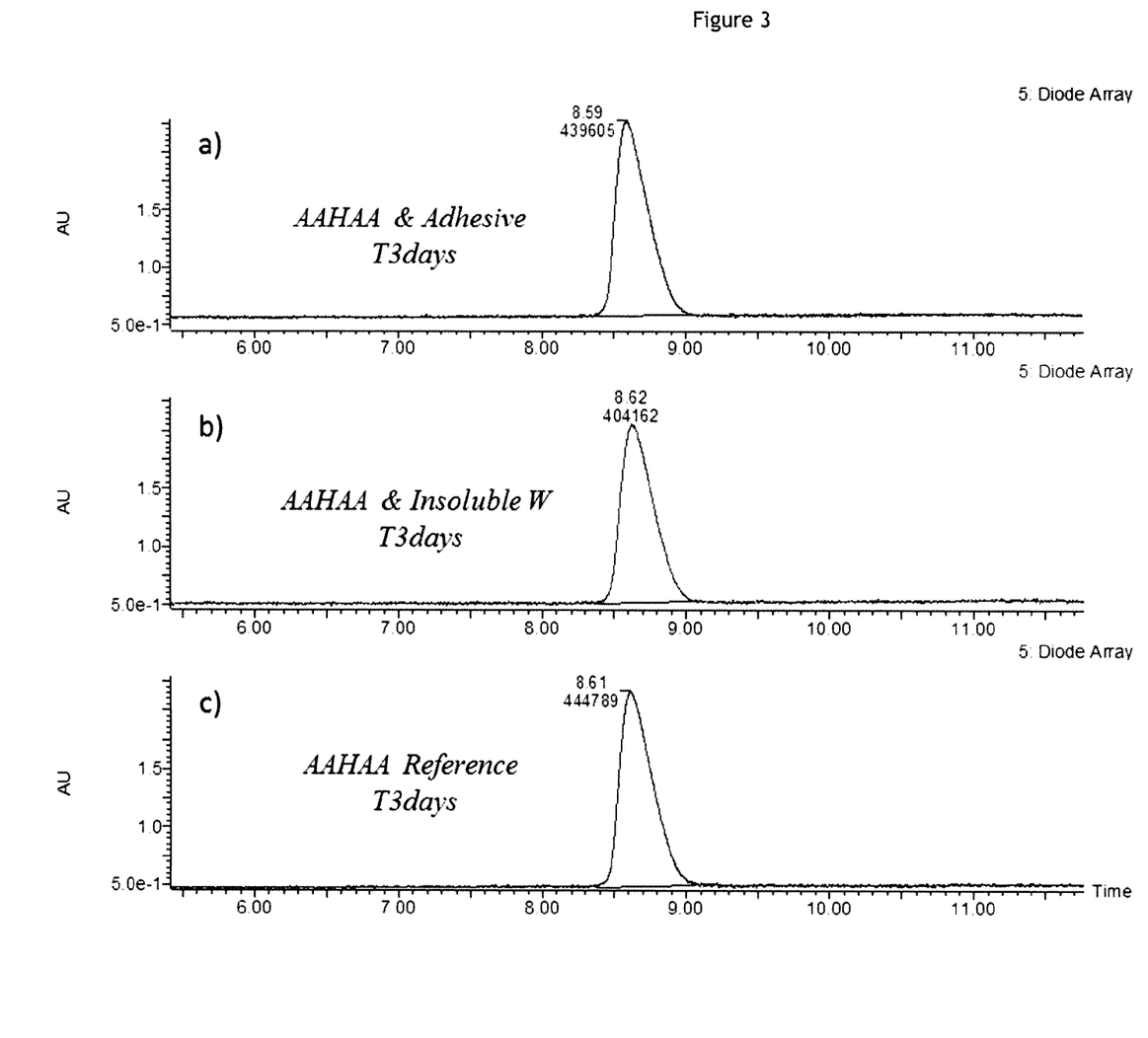
FIG. 3 is AAHAA (SEQ ID NO: 2) peptide ULPC/DAD chromatogram after 3 days at 70° C. in direct contact with two syringe components: (a) adhesive and (b) insoluble tungsten, (c) is the AAHAA (SEQ ID NO: 2) reference.
Figure 4:
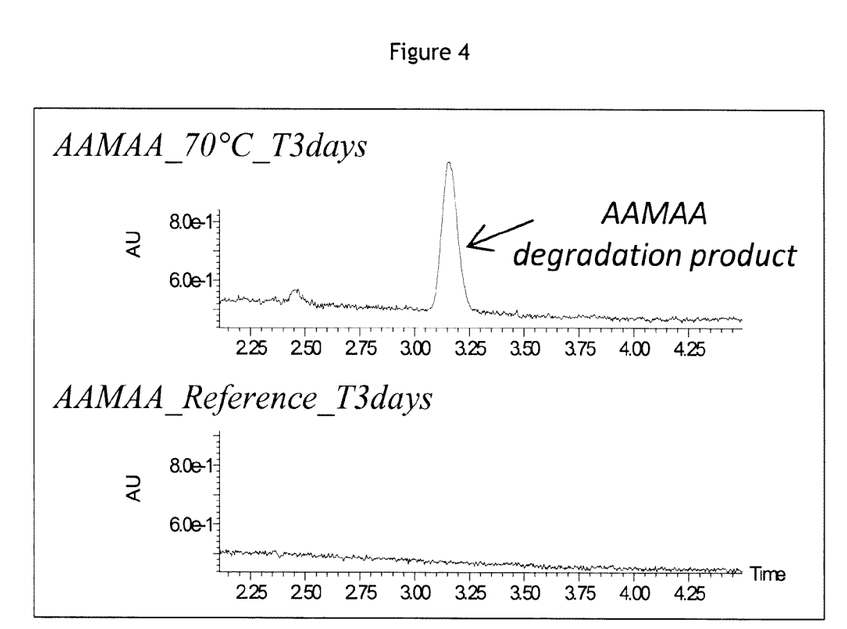
FIG. 4 is the comparison of the degradation profile of AAMAA (SEQ ID NO: 3) peptides when stored in direct contact with ThermoPlastic Elastomer (TPE) tip cap for 3 days at 70° C.

The results are presented on FIG. 3.

FIG. 3 is AAHAA (SEQ ID NO: 2) peptide ULPC/DAD chromatograms after 3 days at 70° C. in direct contact with two syringe components: (a) adhesive and (b) insoluble tungsten. (c) is chromatogram references.

As observed on FIG. 3, AAHAA (SEQ ID NO: 2) peptides react with insoluble tungsten after 3 days at 70° C.

Example 3: Testing of a Tip Cap with Mimetic Peptide No. 3 at High Temperature and Short Duration Time The AAMAA (SEQ ID NO: 3) peptide solutions were dissolved in PBS pH7 buffer (20 mM)+Tween 80 (0.02%) to a final concentration of 45 µg/ml. AAMAA (SEQ ID NO: 3) peptide solutions were stored in direct contact with a TPE tip cap part for 3 days at 70° C.

The invention claimed is:

1. A method to determine the degradation percentage of a compound of formula (I) by contact with part of a container for medical usage, comprising the following successive steps:

i) preparing an aqueous solution comprising a compound of formula (I) below (I)

in which:

$R_1$, $R_2$, $R_4$ and $R_5$ each represent independently of one another H or (C1-C6)alkyl, (C2-C6)alkenyl or (C2-C6) alkynyl;

X represents H or (C1-C6)alkyl, (C2-C6)alkenyl, (C2-C6)alkynyl, (C1-C6) alkoxycarbonyl, aryl, or a protecting group;

n and m each represent independently of one another an integer from 0 to 10;

R3 represents —(CH$_2$)$_2$—COOH, —CH$_2$—COOH, —(CH$_2$)$_4$—COOH, —CH$_2$—OH, —C(OH)—CH$_3$, —CH$_2$—CO—NH$_2$, —CH$_2$—SH, —(CH$_2$)$_4$—NH$_2$, —(CH$_2$)$_2$—CO—NH$_2$, —CH$_2$—CH$_2$—S—CH$_3$, —(CH$_2$)$_3$—NH—C(NH)—NH$_2$;

or $R_3$ represents a group of formula (II) below (II)

where $R_6$, $R_7$, $R_8$ and $R_9$ each represent independently of one another H or (C1-C6)alkyl, (C2-C6)alkenyl or (C2-C6) alkynyl;

X represents H or (C1-C6)alkyl, (C2-C6)alkenyl, (C2-C6)alkynyl, (C1-C6)alkoxycarbonyl, aryl, or a protecting group;

r and p each represent independently of one another an integer from 0 to 10;

ii) adding to the solution prepared at step i) part of a container for medical usage for a period of time of 1 hour to 2 months, at a temperature in a range from 5 to 80° C.;

iii) analyzing by liquid chromatography the solution obtained at step ii); and iv) determining the degradation percentage.

2. The method according to claim 1 further comprising after step iv), a measurement step v) by mass spectrometry and a step vi) of identification of the chemical degradation.

3. The method according to claim 1 wherein $R_1$, $R_2$, $R_4$ and $R_5$ each represent $CH_3$, and X=H, n=1 and m=1.

4. The method according to claim 1 wherein the aqueous solution prepared at step i) comprises from 30 to 100% of water, mass percentage.

5. The method according to claim 1 wherein the aqueous solution prepared at step i) further contains excipients, buffering agents, acids, bases, salts, preservatives, solubilizers, surfactants, chelating agents, sugars, amino acids, peptides, solvents and combinations thereof.

6. The method according to claim 1 wherein the aqueous solution prepared at step i) comprises at least 5 µg/ml of the compound of formula (I).

7. The method according to claim 1 wherein the part of the container for medical usage is a syringe, a prefillable syringe, part of a prefillable syringe, a prefilled syringe or part of a prefilled syringe.

8. The method according to claim 1 wherein the part of the container for medical usage is a barrel, a tip cap, a cap, a needle or a plunger stopper.

9. The method according to claim 1 wherein the part of the container for medical usage is glass, rubber, adhesive, silicon oil, plastic, or metal.

10. The method according to claim 1 wherein the duration of step ii) is in a range from 4 hours to 2 months.

11. The method according to claim 1 wherein step ii) is carried out at a temperature in a range from 15 to 75° C.

12. The method according to claim 10 wherein the duration of step ii) is in a range from 7 days to 45 days.

13. The method according to claim 11 wherein step ii) is carried out at a temperature in a range from 18 to 70° C.

14. The method according to claim 2 wherein the chemical degradation that is identified is oxidation or deamination.

15. The method according to claim 9 wherein the metal is one or more of tungsten or its derivatives, aluminum, boron, silicon, magnesium, zinc, and chrome.

* * * * *

UNITED STATES PATENT AND TRADEMARK OFFICE
CERTIFICATE OF CORRECTION

PATENT NO.        : 11,156,558 B2
APPLICATION NO.   : 16/349761
DATED             : October 26, 2021
INVENTOR(S)       : Claire Brunet et al.

It is certified that error appears in the above-identified patent and that said Letters Patent is hereby corrected as shown below:

In the Claims

Column 16, Line 37-49, Claim 1, delete "" and insert ----

Column 16, Line 53, Claim 1, delete "(C2-C6) alkynyl;" and insert -- (C2-C6)alkynyl; --

Signed and Sealed this
Eighth Day of February, 2022

Drew Hirshfeld
*Performing the Functions and Duties of the
Under Secretary of Commerce for Intellectual Property and
Director of the United States Patent and Trademark Office*